United States Patent
Rüther et al.

[19]

[11] Patent Number: 6,099,510
[45] Date of Patent: Aug. 8, 2000

[54] DEVICE FOR WITHDRAWING A LIQUID FROM A SEALED GLASS AMPOULE

[75] Inventors: Horst Rüther, Hart/Graz; Helmut List; Gerald Kirchmayer, both of Graz, all of Austria

[73] Assignee: AVL Medical Instruments AG, Schaffhausen, Switzerland

[21] Appl. No.: 09/216,845

[22] Filed: Dec. 21, 1998

[30] Foreign Application Priority Data

Dec. 22, 1997 [AT] Austria ..................... 2169/97

[51] Int. Cl.[7] ..................... A61M 5/00
[52] U.S. Cl. ............... 604/181; 604/200; 222/80
[58] Field of Search ............... 604/181, 200, 604/256, 87; 222/80, 541.1, 541.6; 436/49, 48, 54; 422/104, 100, 102

[56] References Cited

U.S. PATENT DOCUMENTS

| 1,680,616 | 8/1928 | Horst . |
| 3,892,237 | 7/1975 | Steiner . |
| 4,417,679 | 11/1983 | Shields ..................... 225/93 |
| 4,506,817 | 3/1985 | Parker . |
| 4,528,268 | 7/1985 | Andersen ..................... 435/31 |
| 4,779,763 | 10/1988 | Klawitter ..................... 222/80 |
| 5,179,024 | 1/1993 | Dahms . |

FOREIGN PATENT DOCUMENTS

| 79279 | 5/1983 | European Pat. Off. . |
| 472457 | 2/1992 | European Pat. Off. . |
| 600508 | 6/1994 | European Pat. Off. . |
| 694498 | 6/1995 | European Pat. Off. . |
| 7216346 | 12/1931 | France . |

Primary Examiner—Wynn Wood Coggins
Assistant Examiner—Kevin C. Sirmons
Attorney, Agent, or Firm—Watson Cole Grindle Watson, P.L.L.C.

[57] ABSTRACT

A device for withdrawing a liquid from a sealed glass ampoule includes a frame holding the sealed glass ampoule in upright or slightly inclined position, such that a tip of the ampoule points upwardly. An element is provided which will press or knock against the side of the tip or neck of the ampoule in order to break the tip of the ampoule in the region of the neck. The device further includes a withdrawing element which can be introduced into the glass ampoule in an area between the bottom of the ampoule and the surface of the liquid therein, and which includes a cannula for withdrawing the liquid.

7 Claims, 2 Drawing Sheets

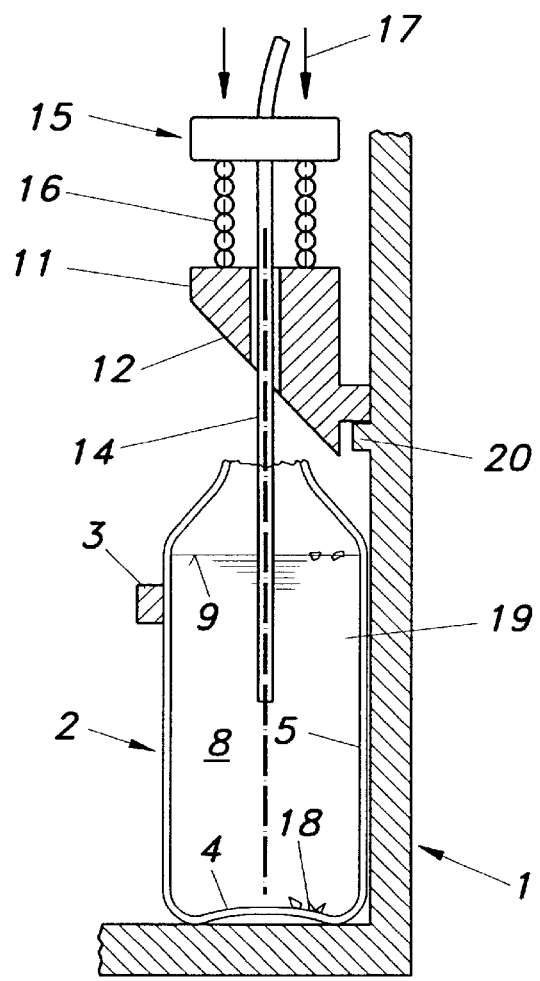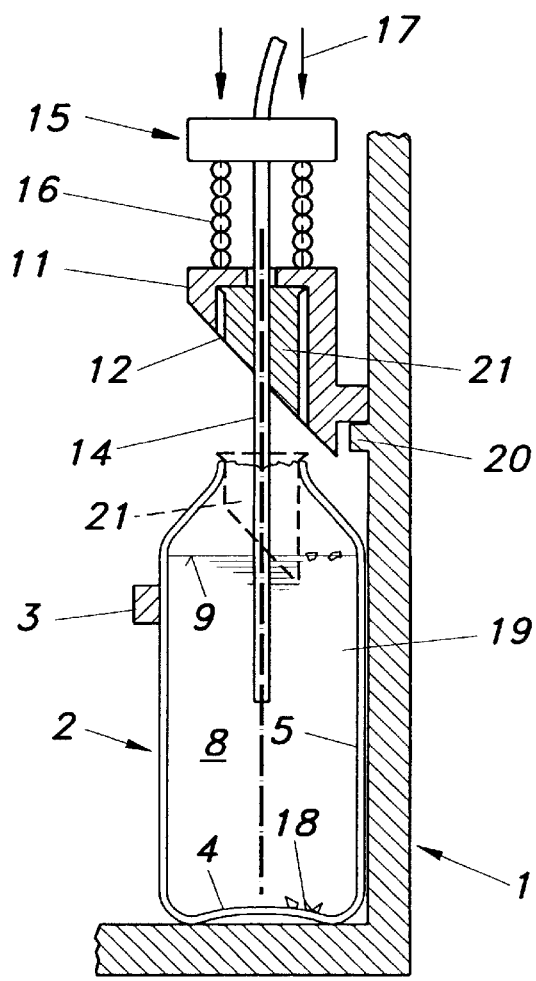

DEVICE FOR WITHDRAWING A LIQUID FROM A SEALED GLASS AMPOULE

BACKGROUND OF THE INVENTION

The invention relates to a device for withdrawing a liquid from a sealed glass ampoule, including a frame in which the sealed glass ampoule is held in upright or slightly inclined position, the tip of the ampoule pointing upwards.

DESCRIPTION OF THE PRIOR ART

In medical laboratories as well as in doctors' practices and hospitals a large number of glass vials or ampoules are handled, which contain a variety of liquids, such as liquid drugs, or liquids for calibration or quality control. Such ampoules must be opened by hand before use.

In a number of applications, especially in the instance of quality control or calibration of laboratory equipment by means of quality control liquids or calibrating media, the manipulations involved in handling such liquids contained in glass ampoules, are far from convenient. Other storage containers suitable for these purposes, however, such as bags or plastic bottles, are undesirable since the gas partial pressures or pH values of the liquids may be subject to changes in the course of prolonged periods of storage, which would render the liquids useless.

In this context U.S. Pat. No. 3,892,237 presents an automatic injecting device with a glass ampoule containing the fluid to be injected. By means of a mechanically actuated element the tip of the ampoule can be broken, which will induce the pressurized content to flow into a vial made of deformable plastic. During injection of the liquid content the plastic vial is deformed by the force of a preloaded spring, and a single-lumen injection needle is ejected from the injection device, which will penetrate into a depth that has been adjusted beforehand. Such a device is not suited for automated processes in laboratory equipment, however.

In EP-A 0 472 457 a device is described for draining vials containing toxic fluids. The small bottles or ampoules consist of perforable material, such as polyethylene, and are held in a rack in upright position the ampoule bottoms facing upwards. Through the perforable bottom of each ampoule a withdrawing element is inserted which has two channels. Through one of these channels a pressurized gas is injected into the bottle, the elastic bottom of the bottle sealing the injection site, thus permitting the build-up of excess pressure in the bottle. Through a second channel in the withdrawing element, whose opening is dipped into the liquid in the ampoule, the toxic content may be pumped off. This device is not suited for use with glass vials, however, nor for calibrating media, since the gas injected into the bottle would change the gas partial pressure of the liquid.

Other devices have been disclosed where the glass ampoule is broken open at the tip or near the bottom, and the liquid contents is drained and collected for further use. The glass ampoule described in FR-A 721 646, for instance, has a conically retracted bottom which may be punctured by a pin-shaped element, such that the liquid contents will flow out.

A similar device is presented in U.S. Pat. No. 1,680,616, where the bottom of a glass ampoule is destroyed by a spike element to release the liquid content. It has been found, however, that there is an interaction between the liquid from the ampoule and the ambient air, such that the actual gas partial pressures will deviate from the target values. Due to the influence of $CO_2$ from the ambient air the liquid's pH may change.

A method and device for the aseptic and splinterfree opening of a sealed glass ampoule are described in EP-A 0079 279, where one end of the ampoule (either tip or bottom) is subjected to the high thermal flow of a gas flame such that the ampoule is melted open in his area. The disadvantage of this procedure is its technical complexity and the unfavorable effects of the gas flame on the liquid contents of the ampoule.

A device for opening a glass ampoule, which is mostly operated by hand, is disclosed in U.S. Pat. No. 4,506,817. The device comprises a hollow cylindrical body into which the tip of a glass ampoule is introduced. Inside the cylindrical body a projecting cutting element will make a scratch in the neck of the ampoule upon rotation of the cylinder, such that the tip of the ampoule may be broken off without running the risk of an injury. The description does not include any information on the automated withdrawal of liquid from the ampoule, however.

In U.S. Pat. No. 5,179,024, finally, a glass ampoule is described, which may be broken open at a rupture mark in the area of the neck, where an elastic sealing ring or sleeve is provided. Upon a slight lateral pressure the tip of the ampoule is broken off at the rupture mark, but is held by the elastic sleeve. Through the sleeve and through the rupture site a syringe may be introduced into the ampoule. The device is not suited for automated withdrawal of the liquid contents of a glass ampoule however.

SUMMARY OF THE INVENTION

It is an object of the invention to propose a device for automatic withdrawal of a liquid, in particular a calibrating or quality control liquid, from a sealed glass ampoule, which will be of a simple mechanical design and prevent changes in liquid parameters, such as ph and gas partial pressures.

In the invention this object is achieved by providing an element which will press or knock against the side of the tip or neck of the ampoule, thus breaking the tip of the ampoule in the region of the neck, in addition to a withdrawing element designed for introduction into the glass ampoule in an area between the bottom of the ampoule and the surface of the liquid, which includes a cannula for withdrawing the liquid. If the liquid is withdrawn quickly enough from an area between the liquid surface and the bottom of the ampoule, it has been found unexpectedly that such important parameters as pH, $pO2$, $pCO2$, will remain virtually unaffected by the influence of the ambient air to which the calibrating or quality control liquid is exposed once the ampoule has been opened. Moreover, since any small glass splinters resulting from breaking open the ampoule will float on the surface of the liquid due to the prevailing surface tension, or sink down to the bottom, splinterfree withdrawal will be possible in this area.

In a variant of the invention which is characterized by great compactness, a translationally movable element is provided, which will slide in the direction of the axis of the glass ampoule, and which has a sloped contact face acting on the side of the ampoule tip, the cannula for liquid withdrawal being guided inside the translationally movable element.

Advantageously, the cannula is supported on the translationally movable element by means of a spring element, the cannula being ready for introduction into the glass ampoule once the translationally movable element has arrived at a stop. In this variant a single translational motion will suffice for the tip of the glass ampoule to be broken off, and for the cannula to overcome the restoring force of the spring element and project from the translationally movable element once the latter has reached the stop, and to be introduced into the glass ampoule.

In order to effectively prevent small glass splinters from being sucked in, a fine-pored filter may be provided at the point or in the lumen of the cannula.

BRIEF DESCRIPTION OF THE DRAWINGS

Following is a more detailed description of the invention as illustrated by the accompanying drawings, in which FIG. 3 shows the device of FIG. 1, after the withdrawing element has been introduced into the glass ampoule, FIG. 4 shows a variant of the device in FIG. 3.

DETAILED DESCRIPTION OF PREFERRED EMBODIMENTS

Figures 1, 1A, 2:
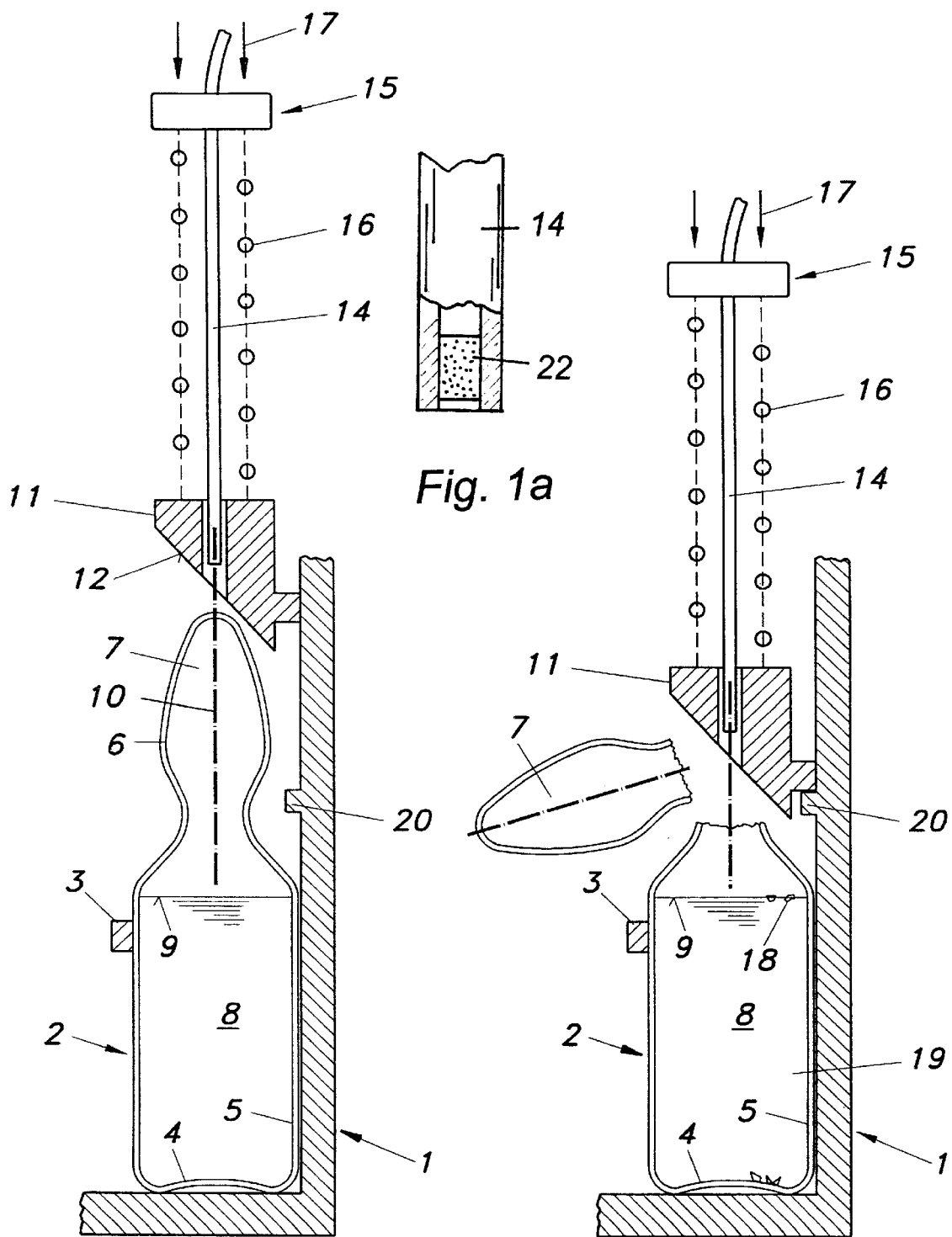
FIG. 1 is an axial section of a device according to the invention, before the withdrawing element is introduced.
FIG. 1a shows a detail of FIG. 1.
FIG. 2 shows the device of FIG. 1, after the tip of the ampoule has been broken off.

The device shown schematically in FIGS. 1 to 3 is provided with a frame 1, in which a glass ampoule 2 is held, preferably elastically, by a support 3. The glass ampoule 2 includes a bottom 4 shaft 5, neck 6 and tip 7, contains a liquid 8 (calibrating or quality control liquid, or liquid drug) with a surface 9. The glass ampoule 2 is in upright position, its tip 7 pointing upwards, but could also be held in a slightly inclined position, by an alternative frame, provided that the neck and tip regions of the ampoule remain free from the liquid. The device is provided with a movable element 11, which is operated by an electromotor pneumatically and slides in the direction of the axis 10 of the glass ampoule 2, and which exhibits a sloped contact face 12 acting laterally on the tip 7 of the ampoule 2. The cannula 14 of a withdrawing element 15 designed for introduction into the glass ampoule 2 is guided in a bore 13.

The cannula 14 of the withdrawing element 15 is supported on the translationally movable element 11 by means of a spring element 16, such that a movement of the withdrawing element 15 along arrows 17 will first of all cause the translational element 11 to move in the direction of the tip 7 of the glass ampoule. During this movement the sloped contact face 12 of the translational element 11 will hit the tip 7 of the glass ampoule 2 laterally, thereby breaking it off (see FIG. 2). Any small glass splinters 18 will partly float on the surface 9, due to the surface tension of the liquid 8, or they will settle at the bottom 4 of the ampoule 2. In this manner a splinterfree zone 19 is created in the liquid 8 after a short waiting period. As shown in FIG. 1a, the lumen of the cannula 14 can containing fine-pored filtering material 22

After the translational element 11 has arrived at a stop 20 of the frame 1, the spring element 16 is compressed by continued application of force along arrows 17, and the cannula 14 of the withdrawing element 15 is introduced into the glass ampoule 2 down to the splinterfree zone 19 (FIG. 3). The liquid 8 may be withdrawn from the glass ampoule 2 by some suction device not shown here. The rapidity of this procedure will ensure that the liquid 8 withdrawn from the splinterfree zone 19 will not be adversely affected by the ambient air acting on its surface.

In the variant shown in FIG. 4 the translational element 11 includes a sealing element 21, which surrounds the cannula 14 and provides a gas-tight seal of the neck of the ampoule 2 once its tip 7 has been removed (see position indicated by broken line). The sealing element 21 is moved along the cannula 14 by means of actuating elements not shown in this drawing. In this variant a partial vacuum is produced in the ampoule 2 by withdrawing liquid 8, such that any fine splinters 18 adhering to the cannula 14 upon withdrawal will be sucked off or removed due to the vacuum or by the sealing element 21.

We claim:

1. A combination of a sealed glass ampoule having a tip, a neck, a shaft and a bottom and containing a liquid, and a device for withdrawing at least some of said liquid from within said sealed glass ampoule; said device comprising a frame for supporting said sealed glass ampoule such that the tip thereof points upwardly, a translationally movable breaking element which is movable toward the sealed glass ampoule along an axis thereof, said breaking element including a sloped contact face for contacting a side of said tip or said neck of said ampoule and separating said tip from said shaft, said breaking element including a bore therein, and a withdrawing element for moving into said glass ampoule to a location between said bottom thereof and a surface of said liquid therein, said withdrawing element including a cannula for withdrawing liquid from within said ampoule, said cannula being movable within said bore in said breaking element.

2. A device according to claim 1, wherein said cannula is supported on said translationally movable element by means of a spring element, said cannula overcoming the force of said spring and being ready for introduction into said glass ampoule once said translationally movable element has arrived at a stop.

3. A device according to claim 1, including a fine-pored filter material in the lumen of said cannula.

4. A device according to claim 1, wherein said translationally movable element includes a sealing element which surrounds said cannula and provides a gas-tight seal at said neck of said ampoule after said tip of said ampoule has been broken off.

5. A combination of a sealed glass ampoule having a tip, a neck, a shaft and a bottom and containing a liquid, and a device for withdrawing at least some of said liquid from within said sealed glass ampoule; said device comprising a frame for supporting said sealed glass ampoule such that the tip thereof points upwardly, a breaking element for contacting a side of said tip or said neck of said ampoule and breaking said ampoule in a region of said neck and separating said tip from said shaft, and a withdrawing element for moving into said glass ampoule to a location between said bottom thereof and a liquid surface therein, said withdrawing element including a cannula for withdrawing liquid from within said ampoule.

6. A device according to claim 5, including a fine-pored filter material in the lumen of said cannula.

7. A device according to claim 5, wherein said translationally movable element includes a sealing element which surrounds said cannula and provides a gas-tight seal at said neck of said ampoule after said tip of said ampoule has been broken off.

* * * * *